US012697086B2

(12) United States Patent
Hatsumi

(10) Patent No.: US 12,697,086 B2
(45) Date of Patent: Aug. 4, 2026

(54) MEDICAL IMAGE CAPTURING SYSTEM

(71) Applicant: FUJIFILM Corporation, Tokyo (JP)

(72) Inventor: Satoru Hatsumi, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 154 days.

(21) Appl. No.: 18/829,303

(22) Filed: Sep. 10, 2024

(65) Prior Publication Data

US 2025/0082296 A1 Mar. 13, 2025

(30) Foreign Application Priority Data

Sep. 11, 2023 (JP) ................................. 2023-147171

(51) Int. Cl.
| | |
|---|---|
| *A61B 6/58* | (2024.01) |
| *A61B 6/00* | (2024.01) |
| *A61B 6/40* | (2024.01) |
| *H05G 1/02* | (2006.01) |

(52) U.S. Cl.
CPC ................ *A61B 6/586* (2013.01); *A61B 6/40* (2013.01); *A61B 6/54* (2013.01)

(58) Field of Classification Search
CPC .. A61B 6/586; A61B 6/40; A61B 6/54; A61B 6/032; A61B 6/00; H05G 1/025; H05G 1/32; H01J 35/08; G01N 27/26; H02B 1/20
See application file for complete search history.

(56) References Cited

U.S. PATENT DOCUMENTS

2013/0285781 A1* 10/2013 Yin .......................... H01F 27/12
977/773
2016/0073485 A1* 3/2016 Kwan ...................... H05G 1/06
378/104

FOREIGN PATENT DOCUMENTS

JP H04252945 9/1992

* cited by examiner

*Primary Examiner* — Courtney D Thomas
(74) *Attorney, Agent, or Firm* — JCIPRNET

(57) ABSTRACT

A medical image capturing system includes: a high-voltage generation device including a tank that accommodates a high-voltage generation unit immersed in first insulation oil; an X-ray tube device including an outer casing that houses a cathode and an anode and a container that accommodates the outer casing immersed in second insulation oil; and a system control device. The system control device calculates a water activity value from a sensor provided in at least one insulation oil. When imaging without warm-up, the system control device presents a tube voltage in a first range if the water activity value is lower than a threshold value, and presents a tube voltage in a second range lower than the tube voltage in the first range if the water activity value is higher than the threshold value. When imaging with warm-up, the high-voltage generation device and/or the X-ray tube device is warmed up.

6 Claims, 10 Drawing Sheets

CHANGES IN OPERATING YEAR OF HIGH-VOLTAGE GENERATION DEVICE FOR X-RAY CT APPARATUS AND WATER ACTIVITY Aw

FIG. 7

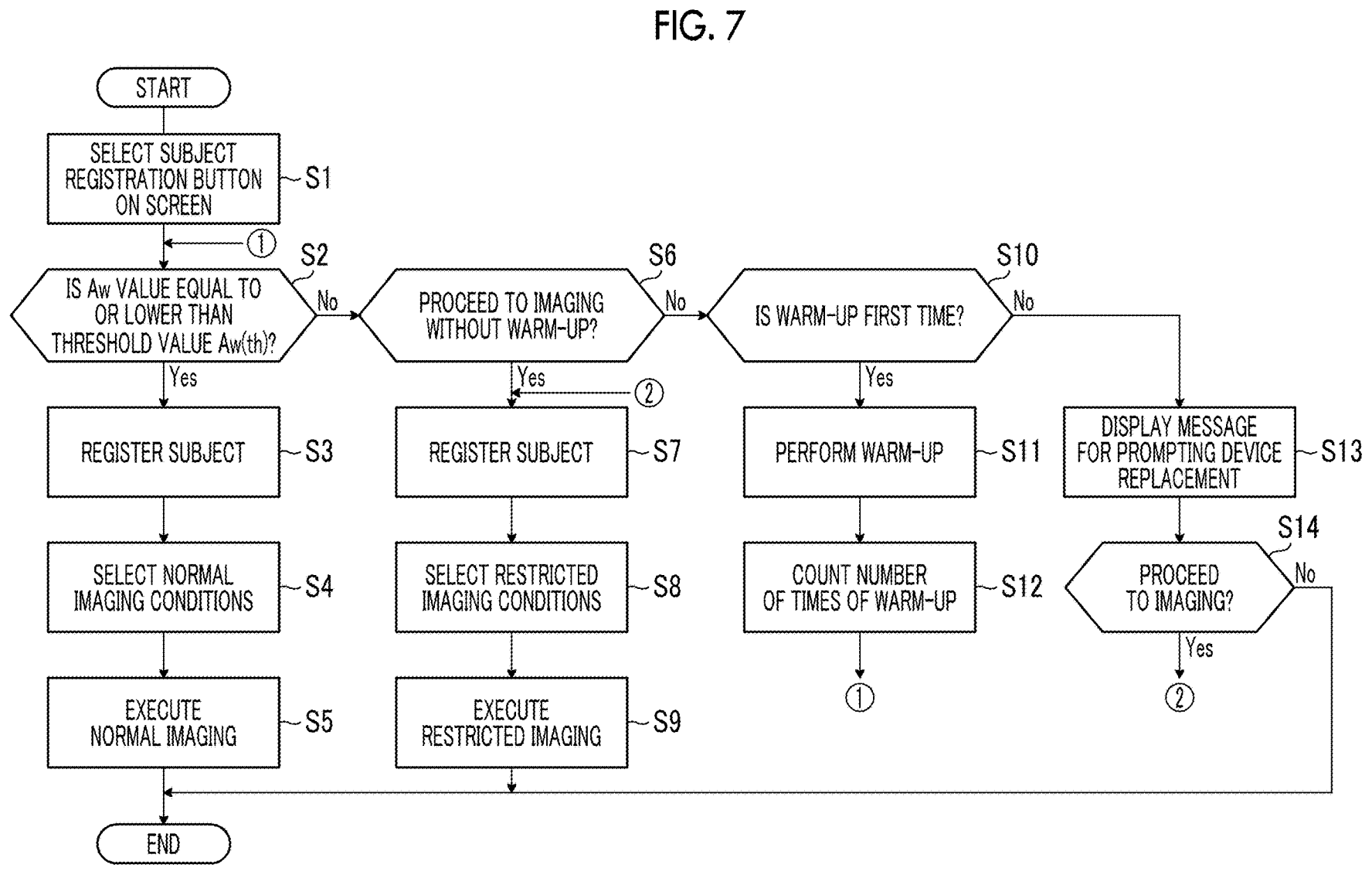

START

S1 — SELECT SUBJECT REGISTRATION BUTTON ON SCREEN

S2 — IS Aw VALUE EQUAL TO OR LOWER THAN THRESHOLD VALUE Aw(th)?

No →

S6 — PROCEED TO IMAGING WITHOUT WARM-UP?

No →

S10 — IS WARM-UP FIRST TIME?

Yes →

S11 — PERFORM WARM-UP

S12 — COUNT NUMBER OF TIMES OF WARM-UP

①

S10 No →

S13 — DISPLAY MESSAGE FOR PROMPTING DEVICE REPLACEMENT

S14 — PROCEED TO IMAGING?

Yes → ②

No →

S6 Yes → ②

S7 — REGISTER SUBJECT

S8 — SELECT RESTRICTED IMAGING CONDITIONS

S9 — EXECUTE RESTRICTED IMAGING

S2 Yes →

S3 — REGISTER SUBJECT

S4 — SELECT NORMAL IMAGING CONDITIONS

S5 — EXECUTE NORMAL IMAGING

END

| SUBJECT ID | | GENDER | |
| --- | --- | --- | --- |
| SUBJECT NAME | | | |
| DATE OF BIRTH | | | |

| kV | PARAMETER 1 | PARAMETER 2 | PARAMETER 3 |
| --- | --- | --- | --- |
| 140 | ○○○ | ○✕○ | ○○○ |
| 120 | ○○○ | ○○✕ | ○○○ |
| 100 | ○△○ | ○✕✕ | ○△○ |
| 80 | ○○□ | ○○□ | ○○□ |

32

PROCEED TO IMAGING WITHOUT WARM-UP?    Yes : No

32

40

| SUBJECT ID | | GENDER | |
| SUBJECT NAME | | | |
| DATE OF BIRTH | | | |

32

44

| kV | PARAMETER 1 | PARAMETER 2 | PARAMETER 3 |
| --- | --- | --- | --- |
| 140 | ○○○ | ○×○ | ○○○ |
| 120 | ○○○ | ○○× | ○○○ |
| 100 | ○△○ | ○×× | ○△○ |
| 80 | ○○□ | ○○□ | ○○□ |

MEDICAL IMAGE CAPTURING SYSTEM

CROSS-REFERENCE TO RELATED APPLICATION

The present application claims priority under 35 U.S.C § 119 (a) to Japanese Patent Application No. 2023-147171 filed on Sep. 11, 2023, which is hereby expressly incorporated by reference, in its entirety, into the present application.

BACKGROUND OF THE INVENTION

1. Field of the Invention

The present invention relates to a medical image capturing system, particularly, a medical image capturing system including a high-voltage generation device and an X-ray tube device that use insulation oil.

2. Description of the Related Art

An X-ray CT apparatus is one of medical image capturing systems. The X-ray CT apparatus is an apparatus that applies X-rays generated by an X-ray tube device to a subject and detects the X-ray dose transmitted through the subject to form an image. A high voltage is applied to the X-ray tube device in order to generate the X-rays. Therefore, in a case in which a large amount of X-rays are generated for a long time, the high-voltage generation device and the X-ray tube device generate a large amount of heat. The X-ray tube device and the high-voltage generation device are filled with the insulation oil in order to ensure the insulation performance and to cool the devices.

The high-voltage generation device and the X-ray tube device are oil-tight, but moisture may enter the insulation oil due to long-term use. For example, the moisture gradually enters through rubber components, such as a rubber packing and a rubber bellows. The entering of the moisture causes a decrease in withstand voltage of the insulation oil, and the necessary insulation performance cannot be maintained, which may lead to discharge and replacement of the device.

For example, JP1992-252945A (JP-H4-252945A) discloses a moisture-in-oil monitoring device that monitors moisture in insulation oil filled in an oil tank of an oil-immersed electrical device such as an oil-immersed transformer or an oil-immersed current transformer. The moisture-in-oil monitoring device includes a moisture-in-oil sensor, and determines an abnormality to output an alarm signal in a case in which a moisture content in the insulation oil exceeds a reference value.

SUMMARY OF THE INVENTION

Meanwhile, in the medical image capturing system that generates the X-rays, an error stop during imaging results in invalid exposure of the subject, and a sudden replacement of the device leads to a loss of the imaging opportunity of the subject. Therefore, it is desired to replace the device before a failure occurs or to continuously use the device by changing imaging conditions such that the discharge does not occur.

The present invention has been made in order to solve the above-described problems, and an object of the present invention is to provide a medical image capturing system that enables continuous use by changing imaging conditions such that discharge does not occur and can prompt device replacement.

A first aspect relates to a medical image capturing system comprising: a high-voltage generation device including a high-voltage generation unit and a tank that accommodates the high-voltage generation unit in a state of being immersed in first insulation oil; an X-ray tube device that applies X-rays, the X-ray tube device including an outer casing that houses a cathode and an anode and a container that accommodates the outer casing in a state of being immersed in second insulation oil; an X-ray detector that detects X-rays transmitted through a subject; and a system control device, in which a moisture-in-oil sensor and a temperature sensor are provided in at least one of the first insulation oil of the high-voltage generation device or the second insulation oil of the X-ray tube device, the system control device calculates a water activity value from a moisture-in-oil content measured by the moisture-in-oil sensor and a temperature measured by the temperature sensor, in a case in which the subject is imaged without warm-up, the system control device presents a tube voltage in a first range in a case in which the water activity value is lower than a threshold value, and presents a tube voltage in a second range lower than the tube voltage in the first range in a case in which the water activity value is higher than the threshold value, and in a case in which the subject is imaged with warm-up, the high-voltage generation device and/or the X-ray tube device including the moisture-in-oil sensor and the temperature sensor is warmed up.

A second aspect relates to the medical image capturing system according to the first aspect, in which, in a case in which the high-voltage generation device and/or the X-ray tube device including the moisture-in-oil sensor and the temperature sensor is warmed up, the system control device operates the high-voltage generation device and/or the X-ray tube device at a voltage lower than a voltage during a normal operation or heats the first insulation oil and/or the second insulation oil with a heater.

A third aspect relates to the medical image capturing system according to the first or second aspect, in which, in a case in which the subject is imaged by warming up the high-voltage generation device or the X-ray tube device, the system control device presents the tube voltage in the first range in a case in which the water activity value is lower than the threshold value, and displays a message for prompting replacement of the first insulation oil and/or the second insulation oil in a case in which the water activity value is higher than the threshold value.

A fourth aspect relates to the medical image capturing system according to any one of the first to third aspects, in which, in a case in which the high-voltage generation device or the X-ray tube device is warmed up, the system control device performs the warm-up before an input imaging reservation time of the subject.

A fifth aspect relates to the medical image capturing system according to any one of the first to fourth aspects, in which the moisture-in-oil sensor and the temperature sensor are provided in the first insulation oil of the high-voltage generation device and the second insulation oil of the X-ray tube device.

A sixth aspect relates to the medical image capturing system according to any one of the first to fifth aspects, in which the medical image capturing system is an X-ray CT apparatus or a radiography apparatus.

According to the aspects of the present invention, the continuous use is enabled by changing imaging conditions such that the discharge does not occur, and the device replacement can be prompted.

BRIEF DESCRIPTION OF THE DRAWINGS

FIG. 7 is a flowchart showing a procedure of processing via the X-ray CT apparatus.

FIGS. 8A and 8B are diagrams showing an example of a screen for subject registration and normal imaging condition selection for normal imaging.

DESCRIPTION OF THE PREFERRED EMBODIMENTS

First Embodiment

As an embodiment of a medical image capturing system according to the embodiment of the present invention, an X-ray computed tomography (CT) apparatus will be described.

Figure 1:
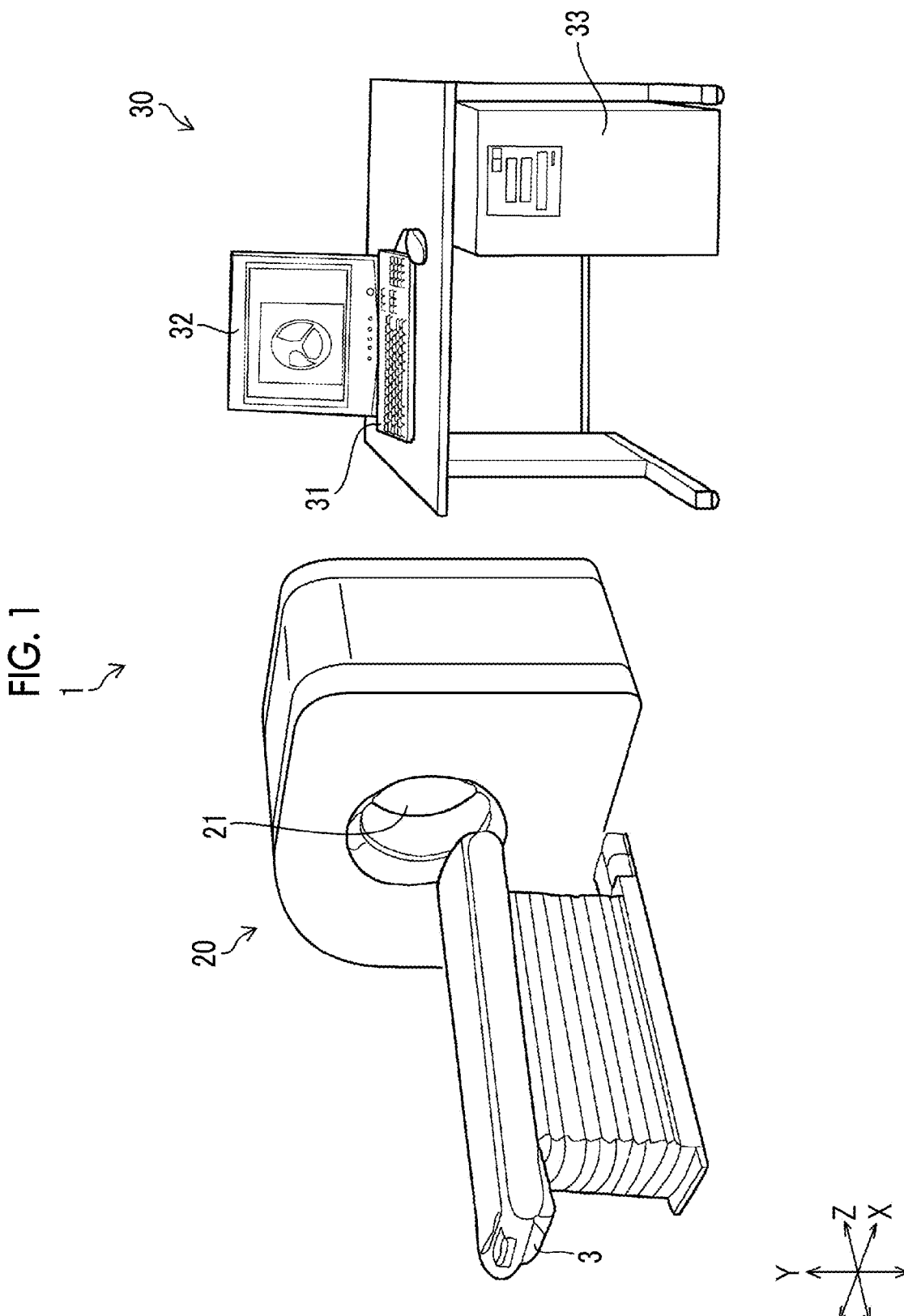
FIG. 1 is a perspective view showing an appearance of an entire X-ray CT apparatus.
Figure 2:
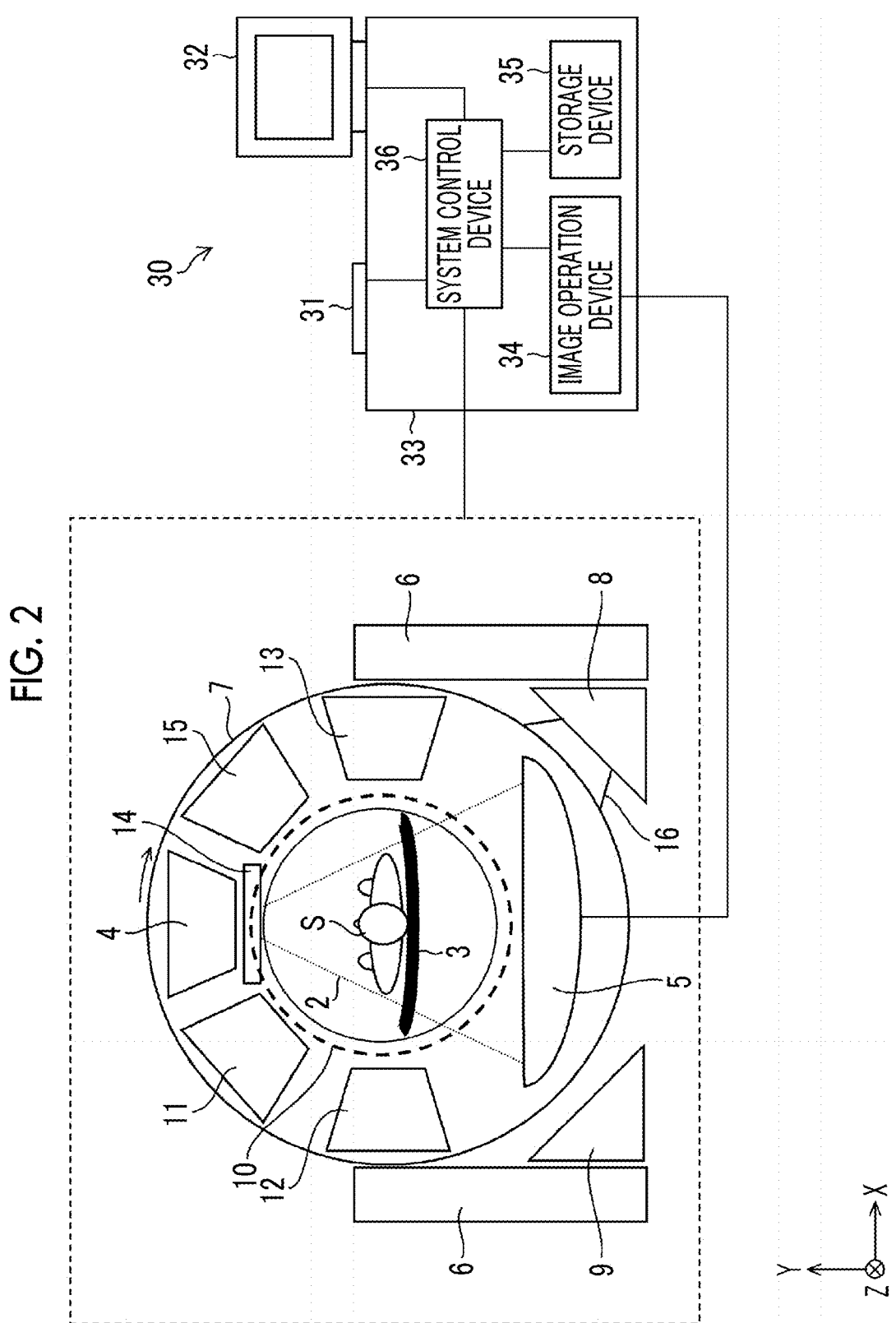
FIG. 2 is a block diagram showing an overall structure of the X-ray CT apparatus according to the embodiment.

An overall structure of an X-ray CT apparatus 1 according to the present embodiment will be described. FIG. 1 is an external view of the X-ray CT apparatus 1, and FIG. 2 is a block diagram showing the overall structure. As shown in FIGS. 1 and 2, the X-ray CT apparatus 1 comprises a gantry 20, an imaging table 3, and an operation unit 30. The gantry 20 has an opening 21 through which the imaging table 3 can pass. The operation unit 30 comprises an input device 31, a display device 32, and a housing 33.

It should be noted that a three-dimensional coordinate system shown in FIGS. 1 and 2 is an example of definition of directions in the X-ray CT apparatus 1. An X axis, a Y axis, and a Z axis of the three-dimensional coordinate system are merely examples and the present invention is not limited thereto. Here, the Z axis direction is a body axis direction of a subject S. The Y axis direction is an up-down direction of the subject S and is a direction parallel to a direction of gravitational force. The X axis direction is a left-right direction of the subject S, and is a horizontal direction orthogonal to the direction of gravitational force.

As shown in FIG. 2, the gantry 20 includes a rotating table 7 comprising the opening 21, a fixed frame (not shown) that supports the rotating table 7 from a back surface side through a bearing (not shown), and a stationary-side stand 6 that supports the fixed frame.

The rotating table 7 is rotatably supported by the fixed frame about a rotation axis. The rotating table 7 is connected to a large pulley (not shown) through a rotation portion side (inner ring) of the bearing. A rotating table control device 8 is fixed at a position close to the stationary-side stand 6. A drive belt 16 is wound around an outer periphery of the large pulley and an outer periphery of a small pulley (not shown) of the rotating table control device 8. The rotating table control device 8 rotationally drives the small pulley, whereby the large pulley rotates through the drive belt 16. A rotational force of the large pulley is transmitted to the rotating table 7 through the inner ring of the bearing, and the rotating table 7 is rotationally driven about the rotation axis. The rotating table control device 8 is a motor.

The rotating table 7 is provided with a plurality of components, such as an X-ray tube device 4, a detector 5, an X-ray control device 11, a high-voltage generation device 12, a scanner control device 13, a collimator 14, and a cooler 15. These plurality of components rotate together with the rotating table 7.

The X-ray tube device 4 is a device that applies X-rays to the subject S placed on the imaging table 3. The collimator 14 is a device that restricts an emission range of X-rays 2 applied from the X-ray tube device 4.

The detector 5 is disposed to face the X-ray tube device 4 on the rotating table 7. The detector 5 is a device that measures a spatial distribution of the transmitted X-rays by detecting the X-rays applied from the X-ray tube device 4 and transmitted through the subject S. The detector 5 has a configuration in which a large number of X-ray detection elements are arranged in the rotation direction of the rotating table 7 or a configuration in which the large number of X-ray detection elements are arranged two-dimensionally in the rotation direction of the rotating table 7 and the rotation axis direction.

The X-ray control device 11 is a device that controls power input to the X-ray tube device 4. The high-voltage generation device 12 applies or supplies a tube voltage and a tube current corresponding to a control signal transmitted from the X-ray control device 11 to the X-ray tube device 4. X-ray conditions, such as the tube voltage and the tube current, are selected or input by an operator from the input device 31 and are determined by a system control device 36. The scanner control device 13 is a device that controls the collimator 14, the detector 5, and the like. The cooler 15 is a device that cools the X-ray tube device 4 to be equal to or lower than a predetermined temperature. The cooler 15 is configured by, for example, a radiator (heat dissipater) and a pump. A DC power supply device 9 generates a DC voltage based on an AC from power supply equipment provided in an examination room or the like. The DC voltage is transmitted to the rotating table 7 through a slip ring 10.

The X-ray tube device 4 is an example of an X-ray tube device according to the embodiment of the present invention. The detector 5 is an example of an X-ray detector according to the embodiment of the present invention. The high-voltage generation device 12 is an example of a high-voltage generation device according to the embodiment of the present invention.

The operation unit 30 comprises an image operation device 34, a storage device 35, and a system control device 36 in the housing 33. The input device 31 is a device for inputting a subject name, an examination date and time, imaging conditions, and the like. Specifically, the input device 31 is a keyboard or a pointing device. The image operation device 34 is a device that performs operation processing on the measurement data detected by the detector 5 to generate a CT image. The display device 32 is a device that displays the CT image generated by the image operation device 34, and is, for example, a liquid crystal display or the like. The storage device 35 is a device that stores the data collected by the detector 5 and the CT image generated by the image operation device 34, and is, for example, a hard disk drive (HDD) or the like. The system control device 36 is a device that controls these devices, the scanner control device 13, the X-ray control device 11, and an imaging table control device (not shown). The system control device 36 is an example of a system control device according to the embodiment of the present invention.

Figure 3:
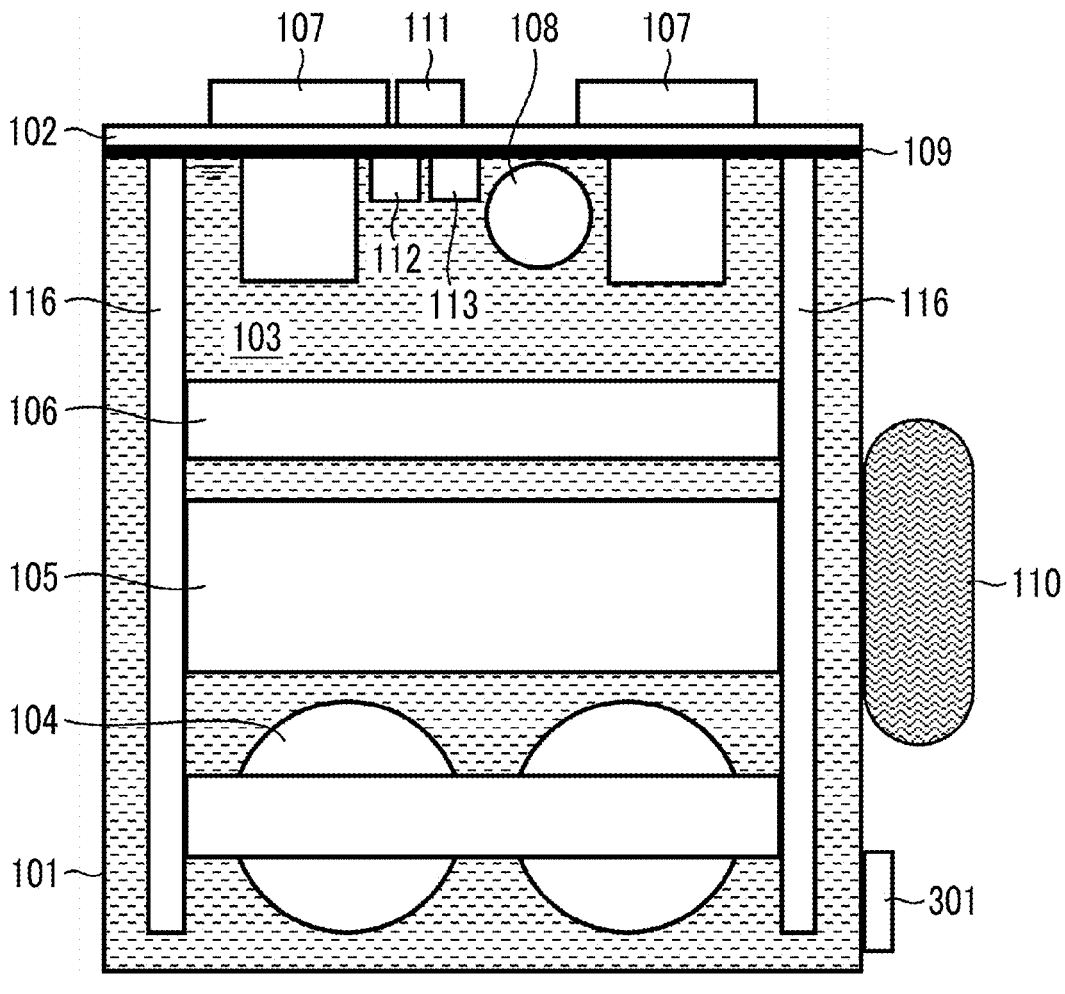
FIG. 3 is a schematic configuration diagram of a high-voltage generation device.

Then, the high-voltage generation device 12 will be described. FIG. 3 is a schematic configuration diagram of the high-voltage generation device 12. As shown in FIG. 3, the high-voltage generation device 12 comprises a tank container 101 and a lid 102 for closing the tank container 101. The lid 102 is disposed on an upper portion of the tank container 101. The high-voltage generation device 12 has a sealed structure by the lid 102 and a rubber packing 109 in order to maintain the oil tightness. The high-voltage generation device 12 comprises a high-voltage transformer 104, a high-voltage rectifier 105, a smoothing capacitor 106, a high-voltage receptacle 107, and a filament transformer 108 inside the tank container 101. The high-voltage transformer 104 boosts an AC voltage input from an AC power supply. The high-voltage rectifier 105 rectifies the output of the high-voltage transformer 104. The smoothing capacitor 106 smoothes the output of the high-voltage rectifier 105. The high-voltage receptacle 107 leads out a high-voltage DC to the outside of the tank container 101. The filament transformer 108 supplies the power to a filament 214 (see FIG. 4) of the X-ray tube device 4. The high-voltage transformer 104, the high-voltage rectifier 105, and the smoothing capacitor 106 are attached to a frame 116. The high-voltage receptacle 107 and the filament transformer 108 are attached to the lid 102.

The tank container 101 of the high-voltage generation device 12 configured as described above is filled with insulation oil 103 that is electrically insulated and serves as a cooling medium. That is, the high-voltage transformer 104, the high-voltage rectifier 105, and the smoothing capacitor 106 are immersed in the insulation oil 103. A rubber bellows 110, which can perform expansion and contraction and communicates with the tank container 101, is attached to a side surface of the tank container 101 in a state of being capable of communicating with the tank container 101. The rubber bellows 110 absorbs the expansion and the contraction due to a temperature of the insulation oil 103.

The tank container 101 is an example of a tank according to the embodiment of the present invention. The high-voltage transformer 104, the high-voltage rectifier 105, and the smoothing capacitor 106 are examples of a high-voltage generation unit according to the embodiment of the present invention. The insulation oil 103 is an example of first insulation oil according to the embodiment of the present invention.

Figure 4:
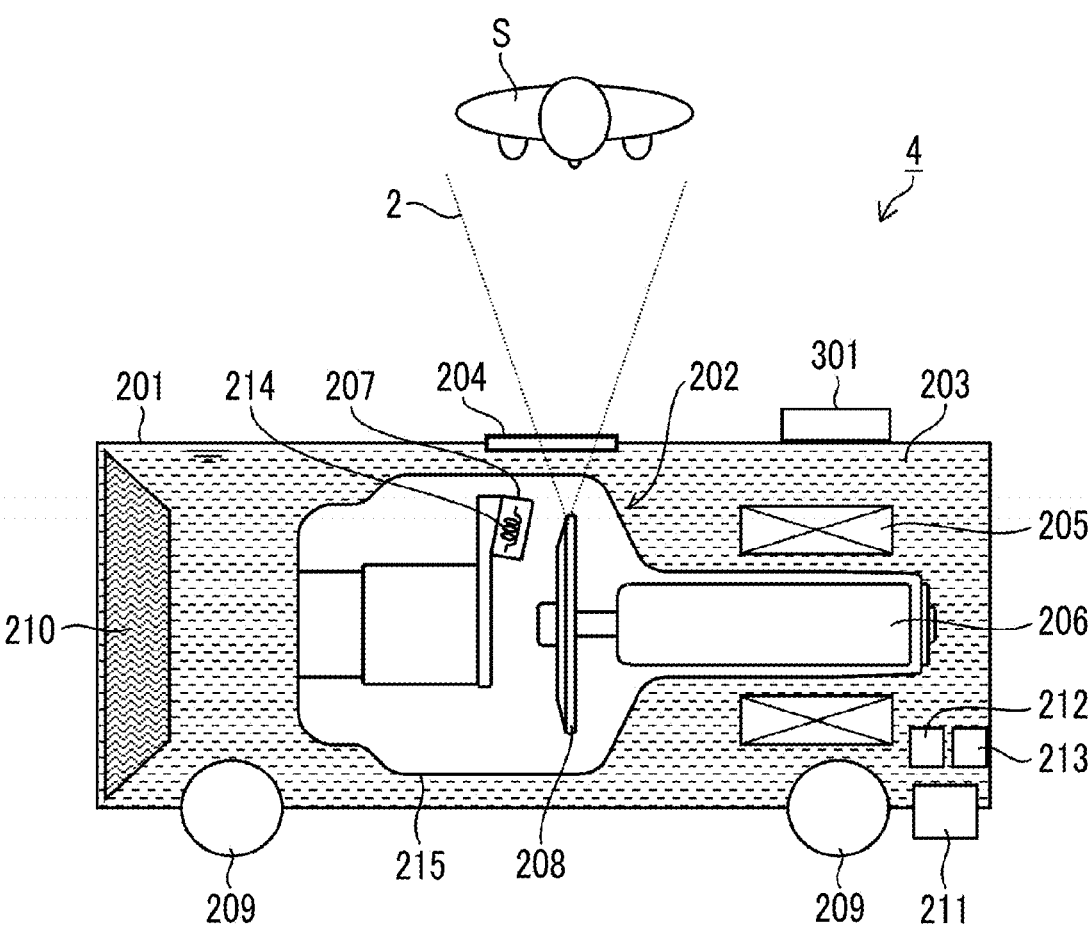
FIG. 4 is a schematic configuration diagram of an X-ray tube device.

Then, the X-ray tube device 4 will be described. FIG. 4 is a schematic configuration diagram of the X-ray tube device 4. As shown in FIG. 4, the X-ray tube device 4 comprises an X-ray tube 202 that generates the X-rays, and an X-ray tube device housing 201 that houses the X-ray tube 202. The X-ray tube 202 is held in a vacuum by the outer casing 215. The outer casing 215 may be a glass tube called a bulb or may be made of a metal, and is used depending on the intended use and the installation position.

The filament 214 and a target 208 provided to face the filament 214 are disposed inside the outer casing 215. The filament 214 emits electrons (electron beams). The target 208 emits the X-rays by being incident with electrons (electron beams) emitted from the filament 214. A cathode of the X-ray tube 202 is composed of the filament 214 which is an electron source, and a converging body 207 that converges the electrons (electron beams) emitted from the filament 214. An anode of the X-ray tube 202 is composed of the target 208 facing the filament 214. The anode is formed as a rotating anode. The target 208 is rotatably supported by a rotating body support mechanism 206. A stator coil 205 rotates a rotor, that is, the rotating body support mechanism 206 and the target 208. The X-ray tube device housing 201 is provided with two high-voltage receptacles 209 for applying the voltage to each of the cathode and the anode. The X-ray tube device housing 201 is filled with insulation oil 203 that is electrically insulated the X-ray tube 202 and serves as a cooling medium. That is, the outer casing 215 is immersed in the insulation oil 203. A rubber bellows 210 that can perform expansion and contraction is attached to a side surface of the X-ray tube device housing 201. The rubber bellows 210 absorbs the expansion and the contraction due to a temperature of the insulation oil 203. The X-ray tube device housing 201 comprises an emission window 204 for emitting the X-rays 2 to the outside of the X-ray tube device 4. The emission window 204 is made of a material having a small atomic number, such as beryllium, and has a high X-ray transmittance.

The X-ray tube device housing 201 is an example of a container according to the embodiment of the present invention. The outer casing 215 is an example of an outer casing according to the embodiment of the present invention. The target 208 is an example of an anode according to the embodiment of the present invention. The filament 214 and the converging body 207 are examples of a cathode according to the embodiment of the present invention. The insulation oil 203 is an example of second insulation oil according to the embodiment of the present invention. It should be noted that the insulation oil 203 may be the same as or different from the insulation oil 103. In the following description, in a case in which the first insulation oil and the second insulation oil do not need to be distinguished from each other, the first insulation oil and the second insulation oil will be simply described as "insulation oil". A type of the insulation oil is not limited, and silicon oil, vegetable oil, or the like can be used.

Then, an operation of the X-ray CT apparatus 1 will be described. The imaging conditions, particularly the tube voltage, the tube current, and the like are input from the input device 31. The rotating table 7 rotates around the subject S. The X-ray control device 11 controls the power input to the X-ray tube device 4 based on the imaging conditions. The X-ray tube device 4 applies the X-rays according to the imaging conditions to the subject S. The detector 5 detects the X-rays, which are applied from the X-ray tube device 4 and transmitted through the subject S, via a large number of X-ray detection elements. A distribution of the transmitted X-rays is measured from a detection result. The data of the CT image is generated by performing various types of processing on the detection result.

Then, a mechanism for generating the X-rays will be described. The input AC voltage on the stationary side is converted into the DC voltage by the DC power supply device 9. The DC voltage is transmitted to the rotating table 7 through the slip ring 10. The DC voltage is converted into a high-frequency AC voltage by the X-ray control device 11 and is converted into the high-voltage DC by the high-voltage generation device 12. The high-voltage DC is applied to the X-ray tube device 4 to generate the X-rays. The X-ray tube device 4 is cooled by the cooler 15.

Then, an operation of the high-voltage generation device 12 will be described. The voltage converted into the high-frequency AC by the X-ray control device 11 is applied to the high-voltage transformer 104 and is converted into a high-frequency high-voltage AC. This voltage is converted into the high-voltage DC by the high-voltage rectifier 105, and is further smoothed by the smoothing capacitor 106 and converted into the high-voltage DC with less ripple. The high-voltage DC is output from the high-voltage receptacle 107 to supply the power to the X-ray tube device 4. The filament transformer 108 supplies the power to the filament 214 of the X-ray tube device 4.

Then, an operation of the X-ray tube device 4 will be described. The high-voltage DC generated by the high-voltage generation device 12 supplies the power to the X-ray tube device 4 through the high-voltage receptacle 209. In addition, the power is also supplied from the filament transformer 108 of the high-voltage generation device 12 to the filament 214 of the X-ray tube device 4, and thermo-electrons for generating the X-rays 2 are generated. The generated thermoelectrons are converged by the converging body 207 and are accelerated toward the target 208 by the supplied high-voltage DC. The X-rays 2 are generated from the target 208 and are applied to the subject S through the emission window 204. In order to prevent the thermoelectrons from being incident on one point of the target 208, the target 208 is rotatably supported by the rotating body support mechanism 206 and is rotated by the stator coil 205.

In the high-voltage generation device 12, moisture may enter from the components such as the rubber bellows 110 and the rubber packing 109 due to long-term use, and the insulation performance of the insulation oil 103 may not be maintained. Similarly, in the insulation oil in the X-ray tube device 4, moisture may enter from the component such as the rubber bellows 210 due to long-term use, and the insulation performance of the insulation oil 203 may not be maintained.

Therefore, in the X-ray CT apparatus 1 according to the embodiment, a temperature sensor 112 and a moisture-in-oil sensor 113 are disposed in the insulation oil 103 of the high-voltage generation device 12. In the X-ray CT apparatus 1, signals of the temperature sensor 112 and the moisture-in-oil sensor 113 can be taken out from a terminal 111 to the outside to monitor the insulation performance of the insulation oil 103. Similarly, in the X-ray CT apparatus 1 according to the embodiment, a temperature sensor 212 and a moisture-in-oil sensor 213 are disposed in the insulation oil 203 of the X-ray tube device 4. In the X-ray CT apparatus 1, signals of the temperature sensor 212 and the moisture-in-oil sensor 213 can be taken out from a terminal 211 to the outside to monitor the insulation oil 203.

The temperature sensor 112 is an example of a temperature sensor according to the embodiment of the present invention. The moisture-in-oil sensor 113 is an example of a moisture-in-oil sensor according to the embodiment of the present invention. The temperature sensor 212 is an example of a temperature sensor according to the embodiment of the present invention. The moisture-in-oil sensor 213 is an example of a moisture-in-oil sensor according to the embodiment of the present invention.

As the moisture-in-oil sensor 113 and the moisture-in-oil sensor 213, a polymer thin film electrostatic capacitance type humidity sensor (HUMICAP: registered trademark) manufactured by Vaisala, a temperature-humidity sensor (MK33-W) manufactured by Innovative Sensor Technology, or the like can be used.

The measurement can be performed by an optical fiber as the temperature sensor 112 and the temperature sensor 212. It is preferable that the inside of the coil can be directly measured.

There is a moisture difference and a temperature difference depending on the location of the high-voltage generation device 12 for the disposition locations of the temperature sensor 112 and the moisture-in-oil sensor 113. Since the high-voltage portion is easily discharged, it is preferable that the temperature sensor 112 and the moisture-in-oil sensor 113 are disposed at the lower portion of the tank container 101 in terms of the improvement in the accuracy. The temperature sensor 112 and the moisture-in-oil sensor 113 may be disposed at two upper and lower portions of the tank container 101.

Then, a relationship between an Aw value of the insulation oil and an insulation withstand voltage of the insulation oil will be described. The high-voltage generation device 12 and the X-ray tube device 4 are filled with the insulation oil for the purpose of suppressing the discharge and cooling the device. However, it is known that, under a condition in which the Aw value (water activity value: humidity of oil) of the insulation oil is high, the discharge is likely to occur. For example, in a case in which the Aw value is 0.4, the dielectric breakdown voltage of the insulation oil is lowered to about 45% as compared with a case in which the Aw value is lower than 0.2. It should be noted that the Aw value is a proportion of the moisture-in-oil content [ppm] to the maximum moisture content (saturated moisture dissolution amount) that can be dissolved in the insulation oil.

The Aw value and the ppm value have a relationship of Expression (1). Here, the values of A and B are inherent values of the insulation oil, and are values different depending on the insulation oil. A and B are values that can be obtained in advance. T is a temperature (K) of the insulation oil.

$$ppm = Aw \times 10^{(B+A/T)} \tag{1}$$

In the high-voltage generation device 12 or the X-ray tube device 4, in a case in which the device is operated and the temperature is raised, the value of the moisture-in-oil content [ppm] is increased. In this case, since the saturated moisture dissolution amount is also high, the Aw value is suppressed in a low state, so that the discharge is less likely to occur.

However, as the temperature of the insulation oil is lowered, the saturated moisture dissolution amount is lowered. On the other hand, since the value of the moisture-in-oil content [ppm] is still high, the Aw value is rapidly increased. In this state, the withstand voltage of the insulation oil is lowered, and the discharge is less likely to occur. In the device that has been used for a long term, there is a possibility that the X-rays are emitted under the maximum tube voltage conditions, which may result in discharge.

Figure 5:
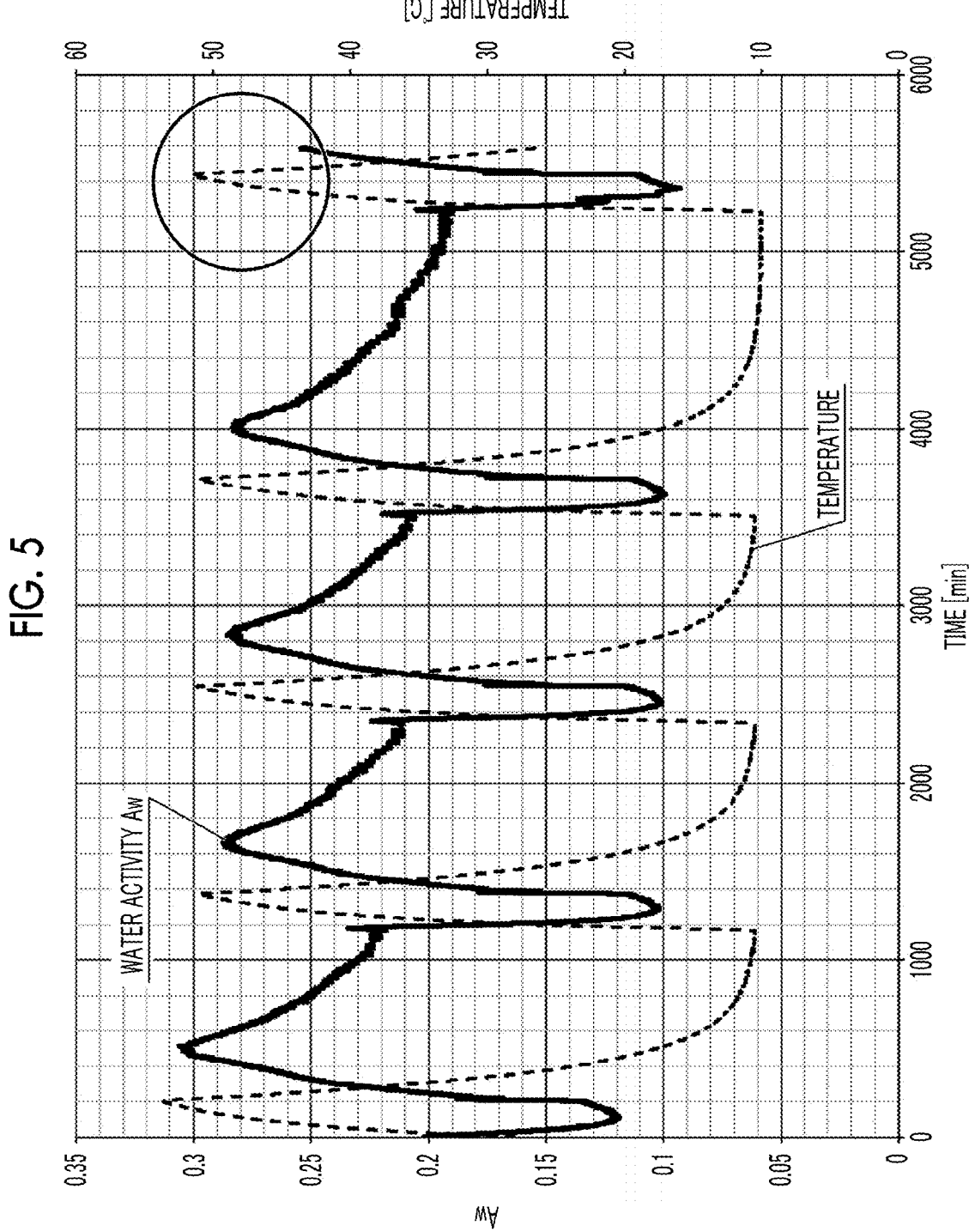
FIG. 5 is a graph showing a relationship among a time, a temperature, and an Aw value.

FIG. 5 is a graph showing a relationship between the temperature, the Aw value, and the time. A horizontal axis represents the time, a left vertical axis represents the Aw value, and a right vertical axis represents the temperature. A solid line indicates the Aw value, and a broken line indicates the temperature. As shown by a portion surrounded by a circle, it can be understood that the Aw value is rapidly increased as the temperature of the insulation oil is lowered. It should be noted that, after the Aw value has reached the peak, the Aw value tends to decrease as the temperature of the insulation oil lowered. It is considered that this is because the temperature of the insulation oil is lowered and the moisture-in-oil content [ppm] also lowered. In a case in which the temperature of the insulation oil is lowered with the elapse of time, the Aw value is also constant.

Figure 6:
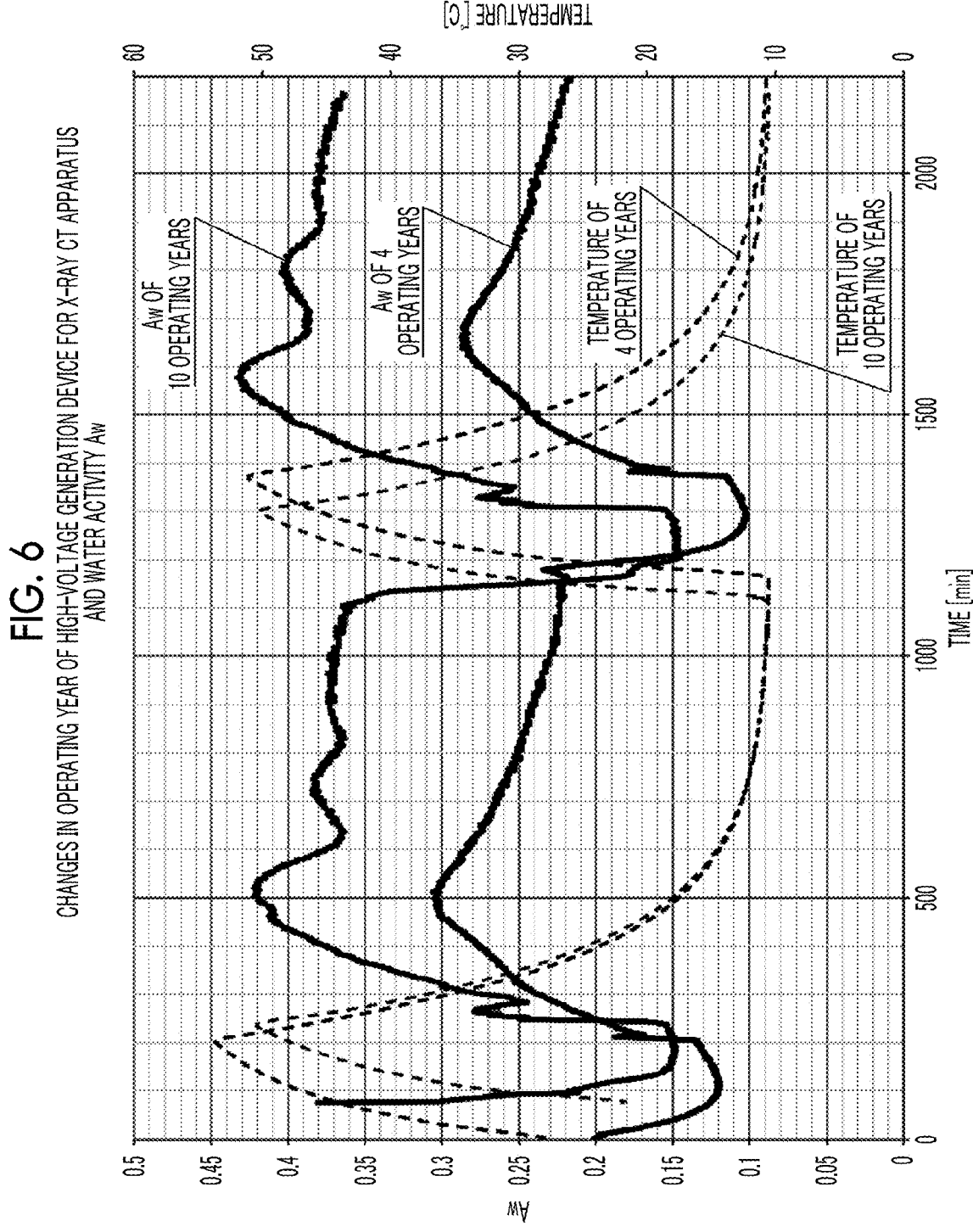
FIG. 6 is a graph showing a relationship between an operating year, a time, a temperature, and an Aw value.

FIG. 6 is a graph showing a relationship between the temperature, the Aw value, the time, and an operating year of the high-voltage generation device. A horizontal axis represents the time, a left vertical axis represents the Aw value, and a right vertical axis represents the temperature. In addition, a solid line indicates the Aw value, and a broken line indicates the temperature. As shown in the graph, the high-voltage generation device having a long operating year tends to have a higher Aw value than the high-voltage generation device having a short operating year. As described above, the discharge is more likely to occur as the Aw value is higher, so that it is preferable to use the high-voltage generation device having a low Aw value in a state of a low temperature.

Therefore, the X-ray CT apparatus 1 according to the embodiment calculates the Aw value of the insulation oil 103 of the high-voltage generation device 12 from the detection results obtained from the temperature sensor 112 and the moisture-in-oil sensor 113. A threshold value Aw(th) for monitoring is set in the X-ray CT apparatus 1. The X-ray CT apparatus 1 can monitor the withstand voltage of the insulation oil 103 of the high-voltage generation device 12 by comparing the calculated Aw value with the threshold value Aw(th).

The X-ray CT apparatus 1 according to the embodiment calculates the Aw value of the insulation oil 203 of the X-ray tube device 4 from the detection results obtained from the temperature sensor 212 and the moisture-in-oil sensor 213. The threshold value Aw(th) for monitoring is set in the X-ray CT apparatus 1. The X-ray CT apparatus 1 can compare the Aw value with the threshold value Aw(th) to monitor the withstand voltage of the insulation oil 203 of the X-ray tube device 4.

The Aw value calculated from the detection results of the temperature sensor 112 and the moisture-in-oil sensor 113 is an example of a first water activity value according to the embodiment of the present invention. The Aw value calculated from the detection results of the temperature sensor 212 and the moisture-in-oil sensor 213 is an example of a second water activity value according to the embodiment of the present invention.

Then, a procedure of processing via the X-ray CT apparatus 1 will be described. FIG. 7 is a flowchart showing a procedure of the processing.

As shown in FIG. 7, the operator selects a subject registration button on the screen (step S1). Specifically, the operator operates the input device 31 to display the registration button on the display device 32. The operator selects the subject registration button on the screen from the input device 31.

Then, it is determined whether or not the Aw value is equal to or lower than the threshold value Aw(th) (step S2). Specifically, the system control device 36 reads out the signals of the temperature sensor 112 and the moisture-in-oil sensor 113 from the terminal 111. The system control device 36 calculates the Aw value of the insulation oil 103 from the temperature T(K) of the temperature sensor 112, the moisture-in-oil content [ppm] of the moisture-in-oil sensor 113, and Expression (1). A and B of the insulation oil 103 are obtained in advance.

The system control device 36 reads out the signals from the temperature sensor 212 and the moisture-in-oil sensor 213 from the terminal 211. The system control device 36 calculates the Aw value of the insulation oil 203 from the temperature T(K) of the temperature sensor 212, the moisture-in-oil content [ppm] of the moisture-in-oil sensor 213, and Expression (1). A and B of the insulation oil 203 are obtained in advance.

The system control device 36 compares the calculated Aw value with the threshold value Aw(th). The system control device 36 determines whether or not the Aw value is equal to or lower than the threshold value Aw(th). In a case in which the Aw value is equal to or lower than the threshold value Aw(th) (step S2: Yes) as a result of this determination, the processing proceeds to step S3.

It should be noted that the same threshold value Aw(th) may be set for the insulation oil 103 and the insulation oil 203, or different threshold values Aw(th) may be set for the insulation oil 103 and the insulation oil 203. In a case in which the Aw value of the insulation oil 103 is equal to or lower than the threshold value Aw(th) and the Aw value of the insulation oil 203 is equal to or lower than the threshold value Aw(th), it can be determined that the Aw value is equal to or lower than the threshold value Aw(th). In other words, the determination can be made in a case in which both the Aw value of the insulation oil 103 and the Aw value of the insulation oil 203 are equal to or lower than the threshold value Aw(th). Since the Aw value is equal to or lower than the threshold value Aw(th), it can be determined that the insulation withstand voltages of the insulation oil 103 and the insulation oil 203 are high.

Then, the operator performs the subject registration (step S3). FIGS. 8A and 8B are diagrams showing an example of a screen for the subject registration and the imaging condition selection. FIG. 8A is an example of a subject registration screen, and FIG. 8B is an example of an imaging condition selection screen. In step S3, in a case in which the operator performs the subject registration, the subject registration screen 40 is displayed on the display device 32. The operator inputs a subject ID, a subject name, a date of birth, and a gender to a subject registration screen 40 from an input device 31.

Then, the operator selects normal imaging conditions (step S4). Specifically, in a case in which the operator performs the subject registration, as shown in FIG. 8B, a normal imaging condition selection screen 42 is displayed on the display device 32. The operator selects the imaging conditions from the input device 31. The normal imaging condition selection screen 42 displays kV (tube voltage) and parameters 1 to 3. In step S2, since it is determined that the Aw value is equal to or lower than the threshold value Aw(th), the operator can select any imaging condition of 80 kV to 140 kV. The parameters 1 to 3 include, for example, other imaging conditions such as the tube current, the imaging part, and the time. 80 kV to 140 kV that can be selected by the operator are examples of a tube voltage in a first range according to the embodiment of the present invention.

Then, the normal imaging is executed (step S5). Specifically, as described regarding the operation of the X-ray CT apparatus 1, in the X-ray CT apparatus 1, the X-ray tube device 4 applies the X-rays according to the normal imaging conditions (tube voltage, tube current, and the like) to the subject S, and generates the image data from the detection result of the X-rays transmitted through the subject S. In a case in which the normal imaging (step S5) ends, the imaging via the X-ray CT apparatus 1 is completed.

Then, in step S2, in a case in which the Aw value is higher than the threshold value Aw(th) (step S2: No), the processing proceeds to step S6.

Figures 9A, 9B, 9C:
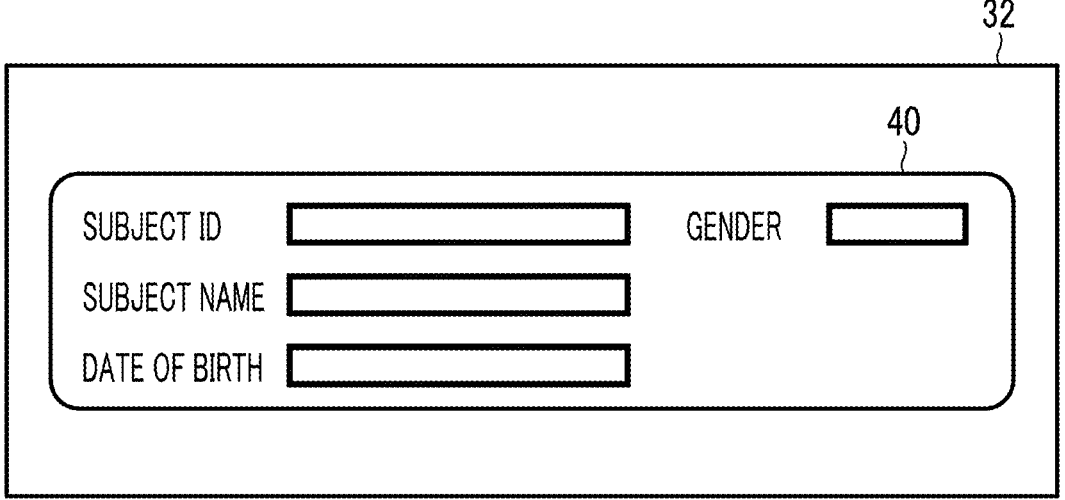
FIGS. 9A to 9C are diagrams showing an example of a screen for subject registration and restricted imaging condition selection for restricted imaging.

Then, it is determined whether or not to proceed to the imaging without the warm-up (step S6). FIGS. 9A to 9C are diagrams showing an example of a screen for the subject registration and the imaging condition selection for restricted imaging. In step S6, specifically, as shown in FIG. 9A, a message "Proceed to imaging without the warm-up?" is displayed on the display device 32. The operator determines whether or not to proceed to the imaging without the warm-up. In a case in which the operator determines to proceed to the imaging without the warm-up (step S6: Yes), the processing proceeds to step S7. In a case of performing the determination, the operator may consider, for example, whether or not the examination of the subject via the X-ray CT apparatus 1 should be urgently executed.

Then, the operator performs the subject registration (step S7). Specifically, as shown in FIG. 9B, similarly to step S3, the operator inputs the subject ID, the subject name, the date of birth, and the gender to the subject registration screen 40 from the input device 31.

Then, the operator selects the restricted imaging conditions (step S8). Specifically, in a case in which the operator performs the subject registration, as shown in FIG. 9C, a restricted imaging condition selection screen 44 is displayed on the display device 32. In the restricted imaging condition selection screen 44, the imaging condition with a high tube voltage (140 kV) is highlighted in a warning color such as red. It should be noted that, in FIG. 9C, the display is performed with a dot pattern. 80 kV to 120 kV that can be selected by the operator are examples of a tube voltage in a second range according to the embodiment of the present invention. In a case in which the selectable maximum tube voltages of the tube voltage in the first range (80 kV to 140 kV) and the tube voltage in the second range (80 kV to 120 kV) are compared with each other, the tube voltage in the second range is lower than the tube voltage in the first range.

In a situation in which the operator selects the restricted imaging conditions, in step S2, it is determined that the Aw value is higher than the threshold value Aw(th). That is, there is possibility that the insulation withstand voltage of the insulation oil 103 or the insulation oil 203 may be lowered, and the discharge occurs.

Therefore, in order to suppress the discharge, the highlight display or the warning display is performed on the restricted imaging condition selection screen 44 such that the operator can avoid selecting the imaging conditions in which the tube voltage is high. The display device 32 can display a message such as "There is possibility of leading to a device failure" as the warning display.

Then, the restricted imaging is executed (step S9). Specifically, in the X-ray CT apparatus 1, the X-ray tube device 4 applies the X-rays according to the restricted imaging conditions (tube voltage, tube current, and the like) to the subject S, and generates the image data from the detection result of the X-rays transmitted through the subject S. In a case in which the restricted imaging (step S9) ends, the imaging via the X-ray CT apparatus 1 is completed. Then, in step S6, in a case in which the operator determines to proceed to the imaging with the warm-up (in step S6: No), the processing proceeds to step S10.

Then, it is determined whether or not the warm-up is the first time (step S10). Specifically, the system control device 36 counts the number of times of the warm-up, and can determine whether or not the warm-up is the first time depending on whether the number of times of the warm-up is 0 or 1 or more. In a case in which the system control device 36 determines that the warm-up is the first time, the processing proceeds to step S11.

Then, the warm-up is executed (step S11). The warm-up is an operation of raising the temperature of the insulation oil 103 to be filled in the high-voltage generation device 12 and/or the insulation oil 203 to be filled in the X-ray tube device 4.

Specifically, the warm-up is executed by operating the high-voltage generation device 12 and/or the X-ray tube device 4 at, for example, a low tube voltage (kV) via the system control device 36. For example, in a case in which the normal operation is set to 100%, in the warm-up, the operation is performed at 15% to 30%. Since the high-voltage generation device 12 and/or the X-ray tube device 4 are operated, the temperature of the insulation oil 103 and/or the insulation oil 203 can be raised. Since the operation is performed at a low tube voltage (kV), there is no need to newly prepare the equipment.

As another warm-up, the insulation oil 103 can be heated by a heater 301 (see FIG. 3) provided in the high-voltage generation device 12 to raise the temperature. In addition, the insulation oil 203 can be heated by the heater 301 (see FIG. 4) provided in the X-ray tube device 4 to raise the temperature.

In a case of using the heater 301, the insulation oil 103 and/or the insulation oil 203 can be heated without emitting the X-rays, and the operator can enter a device room. For example, the heater can be turned on during the preparation for the imaging of the subject, to warm the device while the imaging preparation is performed. The power consumption of the heater 301 is large, but the temperature of the insulation oil 103 and/or the insulation oil 203 can be raised quickly. An induction heating (IH) method heater can be applied to the heater 301.

This warm-up can raise the temperature of the insulation oil 103 to be filled in the high-voltage generation device 12 and/or the temperature of the insulation oil 203 to be filled in the X-ray tube device 4. In a case in which the temperature of the insulation oil 103 and/or the insulation oil 203 is raised, as described above (see FIG. 5), the Aw value of the insulation oil 103 and/or the insulation oil 203 is decreased. By decreasing the Aw value of the insulation oil 103 and/or the insulation oil 203, it is possible to suppress the discharge.

Then, the number of times of the warm-up is counted (step S12). The system control device 36 counts the number of times of the warm-up, and stores the number of times of the warm-up in the storage device 35. Then, the processing proceeds to step S2. In step S2, it is determined whether or not the Aw value of the insulation oil 103 and/or the insulation oil 203 after the warm-up is equal to or lower than the threshold value Aw(th). In a case in which the Aw value is equal to or lower than the threshold value Aw(th), step S3, step S4, and step S5 are executed.

In step S10, in a case in which the warm-up is not the first time (step S10: No), the processing proceeds to step S13.

Then, a message for prompting the device replacement is displayed (step S13). Specifically, in a case in which the system control device 36 determines that the warm-up is not the first time, the system control device 36 causes the display device 32 to display a message such as "Device replacement required".

In a case in which the warm-up is not the first time (step S10: No), even in a case in which the warm-up is performed, the Aw value of the insulation oil 103 and/or the insulation oil 203 is in a state of being higher than the threshold value Aw(th). It can be estimated that the high-voltage generation device 12 and/or the X-ray tube device 4 has a long operating year. Therefore, it is possible to notify the operator that the discharge may occur, by displaying the message for the device replacement.

Then, it is determined whether or not to proceed to the imaging (step S14). The operator determines whether or not to proceed to the imaging. In a case in which it is determined not to proceed to the imaging (step S14: No), the imaging ends, and the device replacement is performed for the high-voltage generation device 12 and/or the X-ray tube device 4. The suppression of the discharge can be achieved by performing the device replacement.

In a case in which it is determined to proceed to the imaging (step S14: Yes), the processing proceeds to step S7. The operator performs the subject registration (step S7), performs the restricted imaging condition selection (step S8), and executes the restricted imaging (step S9). In the restricted imaging condition selection (step S8), in a case in which the warm-up is not the first time, for example, the tube voltage of 140 kV and the tube voltage of 120 kV may be displayed in highlight. Since the Aw value is higher than the threshold value Aw(th) even after the warm-up, there is a risk of discharge. Therefore, in order to avoid the occurrence of the discharge after the warm-up, the tube voltage (imaging condition) may be selectable in a lower range different from the imaging condition in a case in which the warm-up is the first time.

In a case in which the restricted imaging (step S9) ends, the imaging via the X-ray CT apparatus 1 is completed.

Figure 10:
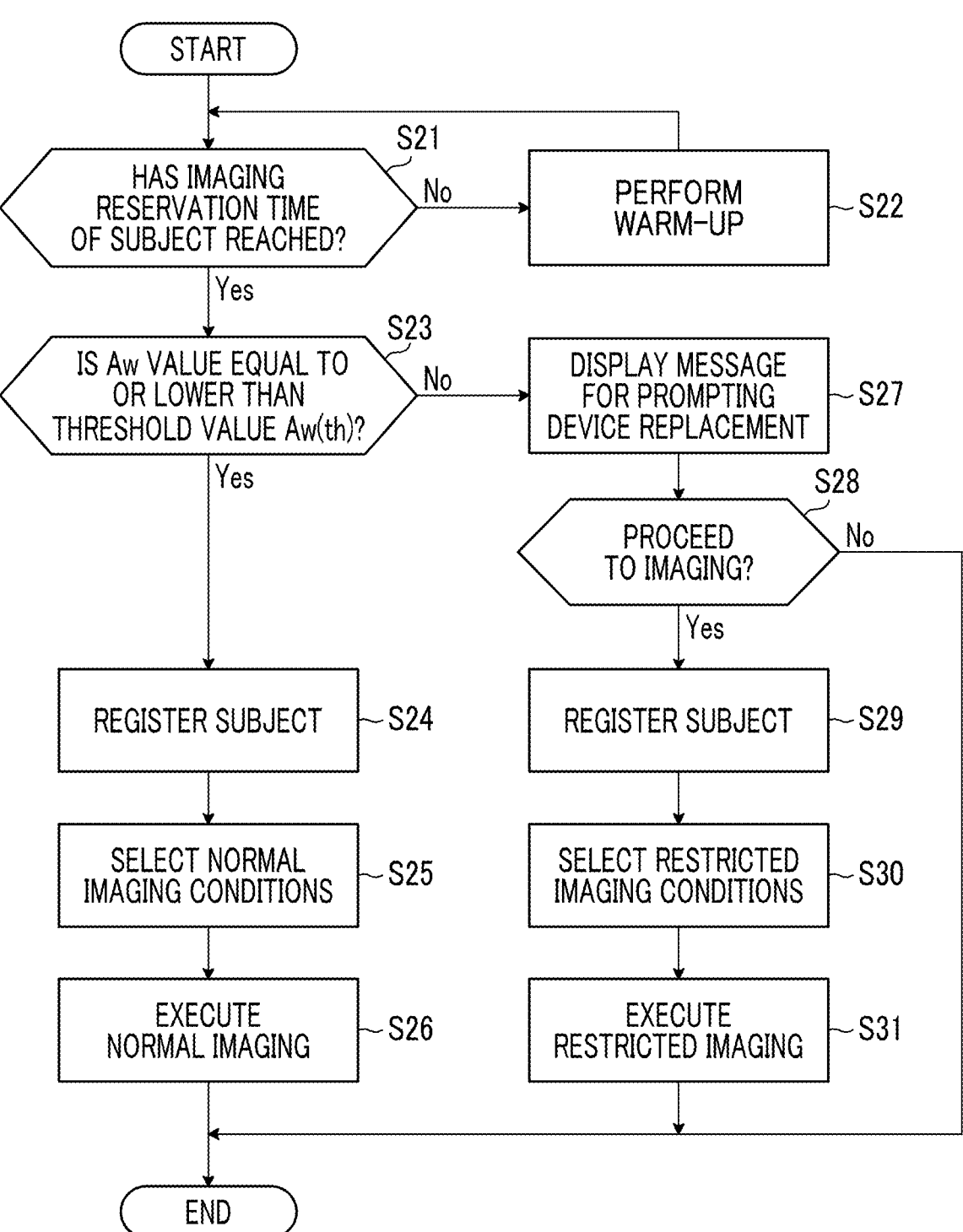
FIG. 10 is a flowchart showing a procedure of processing via the X-ray CT apparatus using an imaging reservation time.

Then, a procedure of the processing of the warm-up via the X-ray CT apparatus 1 using an imaging reservation time will be described. FIG. 10 is a flowchart showing a procedure of the processing.

As shown in FIG. 10, it is determined whether or not the imaging reservation time of the subject has arrived (step S21). Specifically, the system control device 36 compares an imaging scheduled time stored in the storage device 35 with a current time. The system control device 36 calculates a time difference. In a case in which the current time is, for example, before the imaging scheduled time, the system control device 36 determines that the imaging reservation time of the subject has not arrived (step S21: No), and the processing proceeds to step S22. The imaging scheduled time can be set to, for example, 10 minutes before an actual imaging scheduled time. The time such as 10 minutes can be set in advance.

Then, the warm-up is executed (step S22). The warm-up is performed by the same procedure as in step S11. The operator can set a time to perform the warm-up. For example, the operator can set 5 minutes before the actual imaging scheduled time. In a case in which the warm-up ends, the processing proceeds to step S21.

In step S21, in a case in which the time difference between the current time and the imaging scheduled time is shorter than a set time, it is determined that the imaging reservation time of the subject has arrived (step S21: Yes), and the processing proceeds to step S23.

Then, it is determined whether or not the Aw value is equal to or lower than the threshold value Aw(th) (step S23). The determination in step S23 is performed by the same procedure as in step S2. In a case in which the Aw value is equal to or lower than the threshold value Aw(th) (step S23: Yes) as a result of this determination, the processing proceeds to step S24.

Then, the operator performs the subject registration (step S24), performs the normal imaging condition selection (step S25), and executes the normal imaging (step S26). In a case in which the normal imaging (step S26) ends, the imaging via the X-ray CT apparatus 1 is completed. Steps S24, S25, and S26 are performed in the same procedure as in steps S3, S4, and S5.

Then, in a case in which the Aw value is higher than the threshold value Aw(th) (step S23: No) in the determination of step S23, the processing proceeds to step S27.

Then, a message for prompting the device replacement is displayed (step S27). Step S27 is performed by the same procedure as in step S13. In the present flow, since the warm-up is performed before the imaging time is started, in a case of No in step S23, the warm-up is treated in the same manner as in a case of not being the first time, and the processing proceeds to the display of the message for prompting the device replacement (step S27).

Then, it is determined whether or not to proceed to the imaging (step S28). The operator determines whether or not to proceed to the imaging. In a case in which it is determined not to proceed to the imaging (step S28: No), the imaging ends, and the device replacement is performed for the high-voltage generation device 12 and/or the X-ray tube device 4. The suppression of the discharge can be achieved by performing the device replacement.

In a case in which it is determined to proceed to the imaging (step S28: Yes), the processing proceeds to step S29. The operator performs the subject registration (step S29), performs the restricted imaging condition selection (step S30), and executes the restricted imaging (step S31). In a case in which the restricted imaging (step S31) ends, the imaging via the X-ray CT apparatus 1 is completed. It should be noted that, even in a case in which the warm-up is performed before the imaging reservation time, the effect of the warm-up is reduced in a case in which a time difference between the actual imaging time and the warm-up execution time is large. In this case, as the same processing as the processing without the warm-up before the imaging reservation time, the processing procedure of the X-ray CT apparatus 1 can be proceeded according to the flow of FIG. 7.

As described above, with the X-ray CT apparatus 1 according to the first embodiment, the continuous use is enabled by changing the imaging conditions such that the discharge does not occur, and the device replacement can be prompted.

Second Embodiment

In the first embodiment, the case has been described in which the high-voltage generation device 12 comprises the temperature sensor 112 and the moisture-in-oil sensor 113 in the insulation oil 103, and the X-ray tube device 4 comprises the temperature sensor 212 and the moisture-in-oil sensor 213 in the insulation oil 203.

However, the present invention is not limited to this. Only the high-voltage generation device 12 may comprise the temperature sensor 112 and the moisture-in-oil sensor 113 in the insulation oil 103, or only the X-ray tube device 4 may comprise the temperature sensor 212 and the moisture-in-oil sensor 213 in the insulation oil 203.

In a case in which only the high-voltage generation device 12 comprises the temperature sensor 112 and the moisture-in-oil sensor 113 in the insulation oil 103, in step S2 of the flow of FIG. 7, the system control device 36 calculates the Aw value of the insulation oil 103 from the temperature $T(K)$ of the temperature sensor 112, the moisture-in-oil content [ppm] of the moisture-in-oil sensor 113, and Expression (1), and compares the calculated Aw value with the threshold value Aw(th). In step S11, only the high-voltage generation device 12 is warmed up. In addition, in step S23 of FIG. 10, the Aw value of the insulation oil 103 and the threshold value Aw(th) are compared with each other.

Then, in a case in which only the X-ray tube device 4 comprises the temperature sensor 212 and the moisture-in-oil sensor 213 in the insulation oil 203, in step S2 of the flow of FIG. 7, the system control device 36 calculates the Aw value of the insulation oil 203 from the temperature T(K) of the temperature sensor 212, the moisture-in-oil content [ppm] of the moisture-in-oil sensor 213, and Expression (1), and compares the calculated Aw value with the threshold value Aw(th). In step S11, only the X-ray tube device 4 is warmed up. In addition, in step S23 of FIG. 10, the Aw value of the insulation oil 203 and the threshold value Aw(th) are compared with each other.

Therefore, also in the second embodiment, as in the first embodiment, the continuous use is enabled by changing the imaging conditions such that the discharge does not occur, and the device replacement can be prompted.

Others

The function of the system control device 36 is realized by various processors. The various processors include, for example, a CPU and/or a graphic processing unit (GPU) which is a general-purpose processor executing program to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to execute specific processing. The term "program" is synonymous with "software".

One processing unit may be configured by one of these various processors or by two or more processors of the same type or different types. For example, one processing unit may be configured by using a plurality of FPGAs or a combination of a CPU and an FPGA. Moreover, a plurality of processing units may be configured by one processor. A first example of the configuration in which a plurality of processing units are configured by one processor is a form in which one processor is configured by a combination of one or more CPUs and software, and this processor functions as a plurality of processing units, as represented by a computer used in a client or a server. A second example of the configuration is a form in which a processor that implements the functions of the entire system including a plurality of processing units using one integrated circuit (IC) chip is used, as represented by a system on a chip (SoC). As described above, various processing units are configured by using one or more of the various processors as the hardware structure.

It is needless to say that the present invention is not limited to the above-described embodiments and can be variously modified. The medical image capturing system can also be applied to a radiography apparatus other than the X-ray CT apparatus.

EXPLANATION OF REFERENCES

4: X-ray tube device
5: detector
12: high-voltage generation device
36: system control device
103: insulation oil

16

112: temperature sensor
113: moisture-in-oil sensor
203: insulation oil
212: temperature sensor
213: moisture-in-oil sensor
215: outer casing
301: heater
S: subject

What is claimed is:

1. A medical image capturing system comprising:
a high-voltage generation device including a high-voltage generation unit and a tank that accommodates the high-voltage generation unit in a state of being immersed in first insulation oil;
an X-ray tube device that applies X-rays, the X-ray tube device including an outer casing that houses a cathode and an anode and a container that accommodates the outer casing in a state of being immersed in second insulation oil;
an X-ray detector that detects X-rays transmitted through a subject; and
a system control device,
wherein a moisture-in-oil sensor and a temperature sensor are provided in at least one of the first insulation oil of the high-voltage generation device or the second insulation oil of the X-ray tube device,
the system control device calculates a water activity value from a moisture-in-oil content measured by the moisture-in-oil sensor and a temperature measured by the temperature sensor,
in a case in which the subject is imaged without warm-up, the system control device
presents a tube voltage in a first range in a case in which the water activity value is lower than a threshold value, and
presents a tube voltage in a second range lower than the tube voltage in the first range in a case in which the water activity value is higher than the threshold value, and
in a case in which the subject is imaged with warm-up, the high-voltage generation device and/or the X-ray tube device including the moisture-in-oil sensor and the temperature sensor is warmed up.

2. The medical image capturing system according to claim 1,
wherein, in a case in which the high-voltage generation device and/or the X-ray tube device including the moisture-in-oil sensor and the temperature sensor is warmed up, the system control device operates the high-voltage generation device and/or the X-ray tube device at a voltage lower than a voltage during a normal operation or heats the first insulation oil and/or the second insulation oil with a heater.

3. The medical image capturing system according to claim 1,
wherein, in a case in which the subject is imaged by warming up the high-voltage generation device or the X-ray tube device, the system control device
presents the tube voltage in the first range in a case in which the water activity value is lower than the threshold value, and
displays a message for prompting replacement of the first insulation oil and/or the second insulation oil in a case in which the water activity value is higher than the threshold value.

4. The medical image capturing system according to claim 3, wherein, in a case in which the high-voltage generation device or the X-ray tube device is warmed up,
the system control device performs the warm-up before an input imaging reservation time of the subject.

5. The medical image capturing system according to claim 1,
wherein the moisture-in-oil sensor and the temperature sensor are provided in the first insulation oil of the high-voltage generation device and the second insulation oil of the X-ray tube device.

6. The medical image capturing system according to claim 1,
wherein the medical image capturing system is an X-ray CT apparatus or a radiography apparatus.

* * * * *